| United States Patent [19] | [11] Patent Number: 4,540,527 |
| Fields | [45] Date of Patent: Sep. 10, 1985 |

[54] PHOSPHITES AND PHOSPHATES OF 3-SULFOXY-1,2-PROPYLENE GLYCOLS

[75] Inventor: Ellis K. Fields, River Forest, Ill.

[73] Assignee: Standard Oil Company (Indiana), Chicago, Ill.

[21] Appl. No.: 479,699

[22] Filed: Mar. 28, 1983

[51] Int. Cl.³ .......................... C07F 9/09; C07F 9/141
[52] U.S. Cl. .................................. 260/949; 260/948; 252/8.55 R
[58] Field of Search ................................ 260/948, 949

[56] References Cited

U.S. PATENT DOCUMENTS 3,164,624  1/1965  Reed et al. ............................ 260/949
4,081,387  3/1978  Ripple ................................ 260/948

*Primary Examiner*—Anton H. Sutto
*Attorney, Agent, or Firm*—William C. Clarke; William T. McClain; William H. Magidson

[57] ABSTRACT

Phosphites and phosphates of 3-sulfoxy-1,2-propylene glycols are taught as new compositions of matter. These compounds are useful as co-surfactants in enhanced oil recovery.

4 Claims, No Drawings

PHOSPHITES AND PHOSPHATES OF 3-SULFOXY-1,2-PROPYLENE GLYCOLS

FIELD OF THE INVENTION

This invention relates to phosphites and phosphates of 3-sulfoxy-1,2-propylene glycols. More particularly, this invention relates to phosphites and phosphates of 3-sulfoxy-1,2-propylene glycols wherein the said phosphites and phosphates are of the formulas

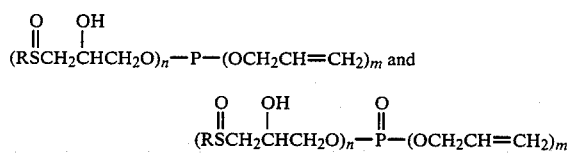

wherein R is selected from the group consisting of an alkyl moiety of 1 to 24 carbon atoms and aryl moieties of 6 to 24 carbon atoms, the ring radicals of said aryl moieties being selected from the group consisting of phenyl, biphenyl, naphthalene, anthracene and phenanthrene radicals, wherein n is 1, 2, or 3; m is 0, 1, or 2; and the sum of n+m is 3.

Preferably R is selected from the group consisting of a phenyl moiety, an alkyl moiety of from 8 to 12 carbon atoms and which is preferably n-octyl to n-dodecyl.

For convenience these compounds are referred to as phosphites and phosphates of 3-sulfoxyl-1,2-propylene glycols. These compounds possess biocidal properties. The invented compounds of molecular weights within the range of from about 400 to about 1000 act as cosurfactants useful in enhanced oil field recovery. These compounds are also useful as surfactants and biocides, and can be used as hydraulic fluids when of sufficiently low molecular weight, and as chemical intermediates.

Cosurfactants function as coupling agents for surfactants and reservoir brines for the purpose of enhancing crude oil production. Surfactant and cosurfactant mixtures are dissolved in brines in low concentrations to form micellar fluids or solutions. These micellar solutions can be described as microemulsions containing surfactants which act to reduce the interfacial tension between water and oil. A second component, a cosurfactant, usually an alcohol, is used to improve the quality of the micellar solution. An efficient cosurfactant increases the micelles' capacity to solubilize more oil or water and still form stabilized solutions.

Compounds used as cosurfactants in the prior art have been alcohols such as isopropyl alcohol, amyl and hexyl alcohols and their ethoxylated derivatives. These cosurfactants have limited capabilities because of the variety of reservoir conditions encountered in enhanced oil recovery programs. For example, special systems must be designed for reservoirs which are essentially fresh water, that is, those which contain 6000 ppm or less monovalent ions, and those which are essentially hard water, those which contain 50,000 ppm monovalent ions plus 500 ppm or more divalent ions. Cosurfactants should perform so as to achieve a stable fluid when the water-cosurfactant mixture is in contact or mixed with crude oil. Molecular weight of the cosurfactant should be sufficiently low to permit passage through semipermeable rock formations and achieve mobility control.

This invention accordingly also relates to a new and unique family of low molecular weight compounds which are suitable for use as cosurfactants for enhanced crude oil recovery. These compounds in use lower the interfacial tension between water and oil, are low molecular weight, of from about 400 to about 1200, and are required in only low concentrations to formulate micellar fluids.

BACKGROUND OF THE INVENTION

Beta-hydroxyalkylsulfoxides to which class the 3-sulfoxy-1,2-propylene glycol phosphites and phosphates of my invention belong, can be prepared by the the method of Anderson, U.S. Pat. No. 3,247,258, which is incorporated by reference, wherein the mercaptan (or thiol), the olefinic compound and oxygen are in contact at temperatures above 80° C. Anderson indicates that with certain olefins and mercaptans such as indene, styrene and thiophenol, the reaction occurs by mixing the olefin and mercaptan first, with the oxygen being bubbled through the mixture thereafter. Other patents such as Oswald, et al., U.S. Pat. No. 3,043,824 and Goodhue, et al., U.S. Pat. No. 3,210,243, which are each incorporated by reference, disclose preparing beta-hydroxyalkylsulfoxides through (1) a co-oxidation route using a hydroperoxide or through (2) oxidation of the sulfide by means of hydrogen peroxide. Oswald indicates that the preparation of hydroperoxide products by olefin-mercaptan co-oxidation to the sulfoxide requires chain initiators, e.g., ultraviolet light and the addition of peroxide compounds (hydroperoxides). In the absence of such catalysts, some co-oxidation reactions have extremely long induction periods and are not practical to carry out. Goodhue teaches that preparation of the sulfoxide using hydrogen peroxide is a three-step synthesis through the sulfide which in turn is prepared from the mercaptan with epichlorohydrin. Fields, in commonly-assigned U.S. Pat. No. 4,040,921, incorporated herein by reference, teaches a one-step process for beta-hydroxyalkylsulfoxides by reacting an olefin and a thiol with oxygen in the presence of a dye sensitizer using visible light at a temperature from −10° C. to 70° C.

The object of this invention accordingly is to produce as new compounds the phosphites and phosphates of 3-sulfoxy-1,2-propylene glycols. These compounds are useful as cosurfactants in enhanced oil recovery, as surfactants and biocides, and as hydraulic fluids when of sufficiently low molecular weight.

SUMMARY OF THE INVENTION

This invention relates to phosphites and phosphates of 3-sulfoxy-1,2-propylene glycols which are useful as cosurfactants in enhanced oil recovery, surfactants and biocides, and as hydraulic fluids when of sufficiently low molecular weight.

DETAILS OF THE INVENTION

The phosphites and phosphates of 3-sulfoxy-1,2-propylene glycols can be prepared by reacting thiols, olefinic phosphites or olefinic phosphates and oxygen according to the method of Fields, U.S. Pat. No. 4,040,921 or by the methods of Anderson, U.S. Pat. No. 3,247,258 or Goodhue, et al., U.S. Pat. No. 3,210,243.

The phosphite and phosphate 3-sulfoxy-1,2-propylene glycols can be aliphatic, aromatic, or heterocyclic beta-hydroxysulfoxides containing substituents such as halo, nitro, cyano, or carboalkoxy groups. They are prepared readily by reacting olefinic phosphites or olefinic phosphates, thiols, and oxygen in the presence of a dye sensitizer and light, according to the equation for the reaction of 1 mole of phosphite with 3 moles of thiol and oxygen:

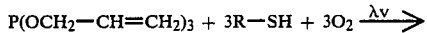

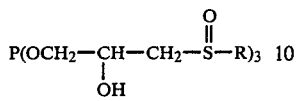

The thiol (or mercaptan) an be aliphatic, aromatic, alicyclic and heterocyclic and can be described as being of the general formula RSH. R can be a moiety of from 1 to 40 carbon atoms. R preferably is a moiety of from 1 to 24 carbon atoms, from methyl to tetracosyl moieties. Examples of such thiols are methylthiol, ethylthiol, n- and isopropylthiol, n-, sec- and tert-butylthiol, n-hexylthiol, n-octylthiol, tert-octylthiol, n-dodecylthiol, n- and tert-hexadecylthiol, cyclohexylthiol, tetracosylthiol, thiophenol, thiocresol, 4-n-dodecylthiocresol, 4-tert-nonylthiocresol, pyridine-2-thiol, pyridine-4-thiol, thiophene-3-thiol, furan-2-thiol, quinoline-2-thiol, quinoline-4-thiol, phenanthridine-1-thiol, 1,3,5,triazine-2-thiol.

Preferably the thiol comprises a thiol containing 1 to 18 carbon atoms. These are preferred because they are cheap, reactive and extend the range of derivatives to cover these solubles in various inorganic and organic solvents. One or more hydrogens of the aliphatic, alicyclic and aromatic moieties such as methyl, ethyl, isobutyl, tolyl and phenyl moieties of the above-described thiol compounds can be replaced with non-reactive radical groups such as halogens and nitro radicals and, on the alicyclic and aromatic moieties, by alkyl moieties.

The molar ratios of the reactants to prepare the 3-sulfoxy-1,2-propylene glycols, i.e., the thiols, olefins, oxygen that can be used, can vary considerably. The thiol-olefin ratio is between 0.001 to 5 moles of thiol per mole of olefin. Substantially equimolar amounts of olefin and thiol are preferred. Use of a solvent such as heptane, hexane, benzene, acetone, or dioxane at concentrations of 1 to 85 weight percent is convenient. When water-miscible solvents such as acetone or dioxane are used, water up to 50% by weight of organic solvent may be incorporated. In such cases, or when water is used with immiscible solvents such as heptane or benzene up to 50% by weight, phase-transfer agents such as cetyl trimethyl ammonium bromide, benzyl triethyl ammonium chloride, benzyl triphenyl phosphonium chloride, etc., are incorporated at concentrations of 0.001 to 1% by weight of total solvent.

Heptane is the preferred solvent: 10 to 40 weight percent is the preferred concentration range of the reactants.

It is essential that at least one optically sensitizing dye be used in conjunction with the application of visible light. The term dye sensitizer can be defined as being an organic dye which increases spectral response. Typical dye sensitizers are fluorescein derivatives, methylene blue, certain porphyrins and polycyclic aromatic hydrocarbons. Suitable dye sensitizers include Rose Bengal, methylene blue and Eosin.

Rose Bengal and methylene blue are the preferred dye sensitizers dissolved in acetone at 0.1-5% by weight. Sufficient dye is added to give final concentrations of 0.02 to 1% by weight in the total reaction mixture; 0.05 to 0.25% by weight is preferred. Alternatively the dye may be introduced bound to an ion-exchange resin in a relatively insoluble form, e.g., anionic Rose Bengal or Eosin attached to the strongly basic anion exchange resin Amberlite IRA-400 (Rohm and Haas, Philadelphia) or cationic methylene blue attached to the strongly acidic cation exchange resin Amberlite IRC-200 (J. R. Williams et al., Tetrahedron Letters, 4603 (1973)).

The reaction may be run in any type of open or sealed vessel, suitably agitated. A particularly useful apparatus for the reaction is the Parr Pressure Reaction Apparatus, Item No. 3911, made by the Parr Instrument Company of Moline, Ill. This apparatus consists of a heavy-walled clear Pyrex bottle connected with a tank of oxygen under pressure; the bottle is shaken vigorously during the reaction. Pressures of oxygen of 1 to 250 psig may be used; 15 to 50 psig $O_2$ are convenient pressures in the laboratory although, commercially, pressures over 100 psig are preferred. The bottle is illuminated with visible light such as ordinary incandescent or photoflood bulbs of 50-500 watts, preferably mounted in reflector with the light source 1½ to 3 inches from the vessel.

The lamps used were General Electric 500 watt photoflood or incandescent bulbs and a General Electric 275 watt sunlamp. Specifications of the G.E. 500 watt photoflood lamp require 1.61 radiated watts from 280 to 400 nanometers, and 6.9 radiated watts from 400 to 700 nanometers, the range of visible light. The G.E. sunlamp has 4.47 radiated watts in the ultraviolet range from 280 to 400 nanometers, and 7.03 radiated watts in the visible light range of 400 to 700 nanometers.

Reaction is continued until the calculated amount of oxygen has been absorbed as shown by pressure drop; times of 1 to 100 hours may be used, depending on the nature of the thiol and the pressure of oxygen. Workup generally consist of evaporating the reaction mixture at 30°-60° C. and 0.1-1 Torr, conveniently in a rotating RINCO evaporator (BUCHI Vacuum Rotary Evaporator ROTAVAPOR EL, Rinco Instrument Company, Inc., Greenville, Ill.).

The present invention also comprises a method of injecting a micellar slug into a subterranean formation comprising the steps of (1) contacting said subterranean formation with an aqueous fluid composition comprising water, a surfactant, a hydrocarbon, an electrolyte and a low molecular weight compound within the range of from about 400 to about 1000 of a beta-hydroxyethyl-sulfoxide; (2) applying sufficient pressure to said composition to cause said micellar slug to move through said formation; (3) maintaining sufficient pressure while injecting said composition into said formation. The said low molecular weight compounds can be selected from the group consisting of phosphites and phosphates of 3-sulfoxy-1,2-propylene glycols.

In order to facilitate a clear understanding of the invention, the process of preparing phosphites and phosphates of 3-sulfoxy-1,2-propylene glycols and the use thereof, the following specific embodiments are described in detail. It should be understood, however, that the detailed expositions of the instant invention, while indicating preferred embodiments, are given by way of illustration only since various changes and modifications within the spirit and scope of the invention will become apparent to those skilled in the art from this detailed description.

PRELIMINARY EXAMPLE

Screening tests for suitable cosurfactants to be used as additives for enhanced oil recovery have been developed which indicate a relationship exists between interfacial tension of the cosurfactant and petroleum removal from core samples using a micellar solution. Surfactant-stabilized dispersions of water in hydrocarbon are micellar solutions. In addition to the required surfactant, water and hydrocarbon micellar solutions can contain cosurfactants and electrolytes to improve stability. Alcohols such as isopropanol and amyl alcohols typically have served as cosurfactants. Sodium chloride and sodium sulfate are examples of electrolytes that are used.

Important aspects of a micellar solution include an ability to solubilize water, compatibility with hydrocarbon and crude oil, an increasing viscosity with increased water concentration and inversion to an oil-in-water solution. In a micelle, surfactant and cosurfactant surround dispersed water which exists in the hydrocarbon phase as spherical droplets. With additional water, the water droplets increase in size. When water is the dispersed phase, the micellar solutions exhibit hydrocarbon-like properties of the external phase. As more and more water is solubilized in a micellar system, spheres enlarge until inversion takes place to form an oil-in-water emulsion. Cosurfactants in a micellar solution stabilize the solution to reduce incidence of inversion and phase separation.

The following bench test has been devised as a preliminary vial screening test to eliminate need for expensive core tests of cosurfactants. The test has been found to have reliability in predicting suitable properties of cosurfactants when used in micellar solutions. The principal important aspect has been found to be the interfacial tension of the cosurfactant in an oil-water mixture. The formulation is required to yield stable fluids in brine and to show low interfacial tension (IFT) as well as very good miscibility with crude petroleum.

Micellar fluids formulated from concentrates containing 40:1 to 5:1 surfactant-cosurfactant ratios have been tested over a wide range of salinities (sodium chloride in water) and hard waters, being examined for phase stability, fluid clarity, interphase behavior and miscibility of aqueous fluids with crude petroleum.

The vial screening bench test is an empirical test which comprises mixing the micellar fluid and crude petroleum by swirling the fluids together in a test tube while observing the interface. A light source is used to observe the fluid-oil behavior. The interfacial mixing (and hence interfacial tension) is judged upon a scale of very low, moderately low, low, medium and high by a comparison with standards previously developed.

For example, brine solutions of a hardness range from under 6,000 ppm of monovalent ions (sodium chloride) to about 50,000 ppm of monovalent ions (sodium chloride) plus 500 ppm of divalent ions (calcium chloride) are mixed with a 40:1 ratio of surfactant-cosurfactant mixture with Second Wall Creek crude. The surfactant is a petroleum sulfonate. Surfactant-cosurfactant-brine mixtures are prepared at ambient temperature and pressure.

Stability of the brine solution with surfactant-cosurfactant mixture is tested by pouring the mixture into a 50 ml graduated cylinder and allowing the solution to stand for one hour undisturbed. Fluids which remained single phase and free of sediment are further tested. 20 ml of solution are poured into a vial. 4 ml of crude petroleum are added to the vial. The vial is turned gently, observing mixing behavior of crude and micellar fluid. The vial is then shaken vigorously for one minute, after which the vial is allowed to stand undisturbed for one hour. After this period, the fluid is evaluated for oil drop-out, number of liquid phases, thickness of emulsion and miscibility. Results are correlated with interfacial tension of solution and crude by visual observation and spinning drop method of J. L. Caylas, et al., "Low Interfacial Tension," American Chemical Society Series No. 8 *Adsorption At Interfaces,* 1975. Formation of round oil droplets which separate quickly, and failure to form an emulsion, indicate a high, ineffective interfacial tension characteristic which can render the cosurfactant unsuitable as an additive for enhanced oil recovery applications.

EXAMPLE I

A mixture of 20.2 g (0.1 mole) of triallyl phosphite, 6.94 ml. of thiophenol, 100 ml of n-heptane, and 10 ml of 0.25 wt% of Rose Bengal in acetone was shaken under 25 psig $O_2$ at 25° C. while being irradiated by a G. E. Sunlamp for 16 hours, during which time 5 lbs. $O_2$ were absorbed. The mixture was filtered, the evaporated to constant weight in a Rinco evaporator at 50° C. and 0.2 torr. The product was a light brown, moderately viscous oil, 33.8 g., 98 mole % yield.

Analysis. Calcd. for $C_{15}H_{21}O_5PS$,

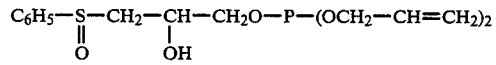

C,52.3; H,6.1; S,9.3; P,9.0. Found: C,52.7; H, 6.0; S,9.6; P,9.2.

The infrared spectrum had a strong absorption band at 3300 cm$^{-1}$ characteristic for —C—OH, and a moderately strong absorption band at 1030 cm$^{-1}$, characteristic of the

stretching frequency. There were only very weak absorptions at 1325 cm$^{-1}$ for P=O, and 980–1080 cm$^{-1}$ for covalent —CH$_2$O—P=O, showing there had been little, if any, oxidation of phosphorus.

EXAMPLES II–XII

Table I lists the results from reacting various mole ratios of mercaptans with triallyl phosphite and triallyl phosphate. Reaction conditions were identical with Example I.

TABLE I

| Example No. | RSH R= | Moles | $O_2$ absorbed, lbs. | Time hrs. | Wt. of Product grams | Yield Mole % |
|---|---|---|---|---|---|---|
| | Triallyl Phosphite Reaction Conditions: | | | | Reaction Products: | |
| II | $C_6H_5$ | 0.2 | 9 | 24 | 46.9 | 97 |
| III | $C_6H_5$ | 0.3 | 13.5 | 72 | 59 | 94 |
| IV | n-$C_8H_{17}$ | 0.1 | 6 | 24 | 36.8 | 97 |
| V | " | 0.2 | 10 | 36 | 52.6 | 94 |
| VI | " | 0.3 | 13.8 | 48 | 72.9 | 99 |

TABLE I-continued

| Example No. | RSH R= | Moles | $O_2$ absorbed, lbs. | Time hrs. | Wt. of Product grams | Yield Mole % |
|---|---|---|---|---|---|---|
| | Triallyl Phosphate | | | | | |
| | Reaction Conditions: | | | | Reaction Products: | |
| VII | $C_6H_5$ | 0.1 | 5 | 15 | 34.3 | 95 |
| VIII | " | 0.2 | 11 | 25 | 44.6 | 89 |
| IX | " | 0.3 | 15 | 72 | 62.2 | 97 |
| X | n-$C_8H_{17}$ | 0.1 | 5 | 48 | 36.1 | 91 |
| XI | " | 0.2 | 11 | 90 | 51.4 | 90 |
| XII | " | 0.3 | 14.8 | 96 | 65.6 | 87 |

Table II gives the elemental analyses of products of Examples II–XII.

TABLE II

| Product of Example # | Emperical Formula | Calcd. C | H | P | S | Found C | H | P | S |
|---|---|---|---|---|---|---|---|---|---|
| II | $C_{21}H_{27}O_7PS_2$ | 51.9 | 5.6 | 6.4 | 13.2 | 52.6 | 5.7 | 6.1 | 13.8 |
| III | $C_{27}H_{33}O_9PS_3$ | 51.6 | 5.3 | 4.9 | 15.3 | 50.1 | 5.7 | 5.0 | 15.2 |
| IV | $C_{17}H_{33}O_5PS$ | 53.7 | 8.7 | 8.2 | 8.4 | 53.0 | 8.9 | 7.7 | 7.9 |
| V | $C_{25}H_{51}O_7PS_2$ | 53.8 | 9.1 | 5.6 | 11.5 | 54.2 | 9.4 | 5.7 | 11.8 |
| VI | $C_{33}H_{69}O_9PS_3$ | 53.8 | 9.4 | 4.2 | 13.0 | 54.7 | 9.4 | 4.8 | 12.7 |
| VII | $C_{15}H_{21}O_6PS$ | 50.0 | 5.8 | 8.6 | 8.9 | 49.7 | 5.9 | 8.4 | 9.1 |
| VIII | $C_{21}H_{27}O_8PS_2$ | 50.2 | 5.4 | 6.2 | 12.7 | 50.7 | 5.8 | 6.1 | 13.1 |
| IX | $C_{27}H_{33}O_{10}PS_3$ | 50.3 | 5.1 | 4.8 | 14.9 | 50.7 | 5.6 | 4.3 | 15.1 |
| X | $C_{17}H_{33}O_6PS$ | 51.5 | 8.3 | 7.8 | 8.1 | 50.9 | 8.6 | 8.5 | 8.4 |
| XI | $C_{25}H_{51}O_8PS_2$ | 52.3 | 8.9 | 5.4 | 11.1 | 52.6 | 9.4 | 5.7 | 11.5 |
| XII | $C_{33}H_{69}O_{10}PS_3$ | 52.7 | 9.2 | 4.1 | 12.8 | 52.6 | 9.6 | 4.4 | 13.1 |

The products were dark yellow to brown viscous oils. All showed the —C—OH band at 3300 cm$^{-1}$ and the —S=O band at 1030 cm$^{-1}$ in the infrared spectra. The absorption of the products from Examples II–VI showed weak absorption at 1325 cm$^{-1}$ and 980–1080 cm$^{-1}$ for P=O and $CH_2O$—P=O, respectively. In contrast, the products of Examples VII–XII had very strong absorption at 1325 cm$^{-1}$ and 980–1080 cm$^{-1}$.

EXAMPLE XIII

Interfacial tension of compounds of Examples I to XII were determined at 1 (wt)% concentration between solvent-extracted 5W oil and water, using a Cenco-Du Nouy Interfacial Tensiometer No. 70545 with a 6 cm platinum-iridium ring at 25° C. with a double distilled water, with these results:

| Product of Example # | Interfacial Tension, dynes/cm |
|---|---|
| Control | 41.73 |
| I | 8.74 |
| II | 8.46 |
| III | 9.39 |
| IV | 9.30 |
| V | 7.28 |
| VI | 9.30 |
| VII | 18.81 |
| VIII | 16.88 |
| IX | 6.95 |
| X | 4.20 |
| XI | 11.09 |
| XII | 16.30 |

In the phosphite series Examples I–VI there was little variation in surfactant properties, whereas in the phosphate series, Examples VII–XII, increasing the mole ratio of phenylsulfoxide content increased surface activity, and increasing octyl sulfoxide content decreased surface activity.

EXAMPLE XIV

Compounds of Examples I to XII were tested in the vial test as cosurfactant for enhanced oil recovery, using 5% petroleum sulfonate as surfactant in 0.8N brine (NaCl), adding the cosurfactant to surfactant at a ratio of 1:20, and noting the stability of the mixture, as brine tends to cause the surfactant to separate (salt) out. The brine-surfactant-cosurfactant mixture, 20 ml, was then mixed by shaking with 2.5 ml of crude petroleum and the interfacial tension (IFT) observed. Low IFT was indicated by easy mixing of the two phases with no separation. Formation of round oil droplets that separate quickly indicates a high, ineffective IFT.

Products of Examples I through VI and IX, X and XI proved effective in lowering the IFT in the vial test, giving mixtures of brine-surfactant-cosurfactant fluids which were stable, did not separate, and easily formed mixtures of the fluid with crude petroleum. Products of Examples VII, VIII and XII were poor.

EXAMPLE XV

Control of microorganisms in inhibiting or preventing growth of fungi in enhanced oil recovery operations is a desirable characteristic of useful additives.

The products of this invention was tested as biocides and inhibitors for the growth of microorganisms by this test: 25 g of agar preparation were placed in standard Petri dishes. The agar preparation consisted of 23.5 g of Bacto Plate Count Agar, Difco Laboratories, Detroit, Mich., dissolved in 1 liter of water. Plate Count Agar contains a standard USP formula for nutrient agar, consisting of 5 g: Pancreatic digest of casein
2.5 g: Yeast extract
1 g: Glucose
15 g: Agar Four petri dishes were untreated and used as blanks. To the others, in duplicate, were added 2.5 ml of 1% acetone solutions of the products of Examples I-XII. All plates were uncovered for 4 hours to expose them to the spores of adventitious fungi and bacteria, then covered and stored at 30° C. for 6 days. Ratings were given at this point; 0 represents no growth, 5 shows luxuriant colonies of fungi and bacteria. Results were as follows:

| Product of Example No. | Rating |
|---|---|
| I | 0,0 |
| II | 0,0 |
| III | 0,0 |
| IV | 0,0 |
| V | 0,0 |

| Product of Example No. | Rating |
| --- | --- |
| VI | 0,0 |
| VII | 0,0 |
| VIII | 2,1 |
| IX | 0,0 |
| X | 3,2 |
| XI | 0,0 |
| XII | 0,0 |
| Control | 5,5,5,5 |

The products of this invention as EP additives, surfactants, and biocides, can be used in solutions and formulations at concentrations of 0.001% to 10% by weight.

EXAMPLE IX

A micellar slug for micellar flooding consisting of 3 (vol)% petroleum sulfonate as surfactant, 2 (vol)% petroleum hydrocarbon, 1 (vol)% cosurfactant comprising a phosphate of a beta-hydroxyethylsulfoxide prepared from triallyl phosphate and thiophenol, molecular weight 644, in a 1.0N NaCl brine solution is prepared. The micellar slug fluid is fed into the high pressure injection pump and is injected into a 25 foot section sandstone formation in Crawford County, Ill., USA, through an injection well at 900 psig. The amount of slug injected is about 7% of reservoir pore volume and the petroleum hydrocarbon is lease crude oil. Pattern of injection is two rows of injection wells and three rows of producer wells. There are nine wells in each row and total area enclosed is 40 acres. Injection and production wells are 460 feet apart and adjacent walls are 115 feet apart. Crude oil production increases to recover about 30% of the oil in place at start of the injection.

What is claimed is:

1. A composition of the structural formula

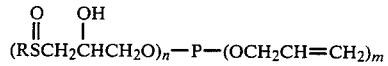

wherein R is selected from the group consisting of an alkyl moiety of 1 to 24 carbon atoms, aryl moieties of 6 to 24 carbon atoms, the ring radicals of said aryl moieties being selected from the group consisting of phenyl, biphenyl, naphthalene, anthracene and phenanthrene radicals, wherein n is a whole number from 1 to 3, m is selected from the group of numbers consisting of 0, 1 and 2, and the sum of n+m is 3.

2. The composition of claim 1 wherein R is selected from the group of moieties consisting of methyl, ethyl, n-octyl, n-dodecyl, tert-octyl, tert-dodecyl, phenyl and cresyl moieties.

3. A composition of the structural formula

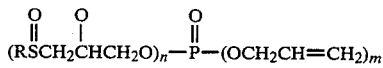

wherein R is selected from the group consisting of an alkyl moiety of 1 to 24 carbon atoms and aryl moieties of 6 to 24 carbon atoms, the ring radicals of said aryl moieties being selected from the group consisting of phenyl, biphenyl, naphthalene, anthracene and phenanthrene radicals, wherein n is a whole number from 1 to 3, m is selected from the group of numbers consisting of 0, 1 and 2, and the sum of n+m is 3.

4. The composition of claim 3 wherein R is selected from the group of moieties consisting of methyl, ethyl, n-octyl, n-dodecyl, tert-octyl, tert-dodecyl, phenyl and cresyl moieties.

* * * * *